United States Patent [19]

Baggiolini et al.

[11] Patent Number: 4,804,502
[45] Date of Patent: Feb. 14, 1989

[54] VITAMIN D COMPOUNDS

[75] Inventors: Enrico G. Baggiolini, North Caldwell; John J. Partridge, Upper Montclair; Shian-Jan Shiuey, Nutley; Gary A. Truitt, Bloomfield; Milan R. Uskokovic, Upper Montclair, all of N.J.

[73] Assignee: Hoffmann-La Roche Inc., Nutley, N.J.

[21] Appl. No.: 145,867

[22] Filed: Jan. 20, 1988

[51] Int. Cl.[4] .............................................. C07J 9/00
[52] U.S. Cl. .................................................. 260/397.2
[58] Field of Search ............... 568/816, 817, 832, 834, 568/838; 260/397.2

[56] References Cited

U.S. PATENT DOCUMENTS 4,358,406 11/1982 Deluca et al. ..................... 260/397.2
4,521,410 6/1985 Holich et al. ..................... 260/397.2
4,689,180 8/1987 Deluca et al. ..................... 260/397.2

Primary Examiner—Werren B. Lone
Attorney, Agent, or Firm—Jon S. Saxe; Bernard S. Leon; Matthew Boxer

[57] ABSTRACT

Compounds of the formula

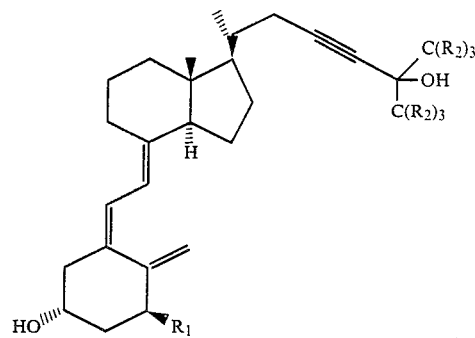

wherein $R_1$ is hydrogen or hydroxy and $R_2$ is hydrogen or fluorine are described. The compounds of formula I are useful as agents in the treatment of disease states characterized by metabolic calcium deficiencies. Examplary of such disease states are osteoporosis and renal osteodystrophy.

15 Claims, No Drawings

VITAMIN D COMPOUNDS

BRIEF SUMMARY OF THE INVENTION

The invention is directed to compounds of the formula

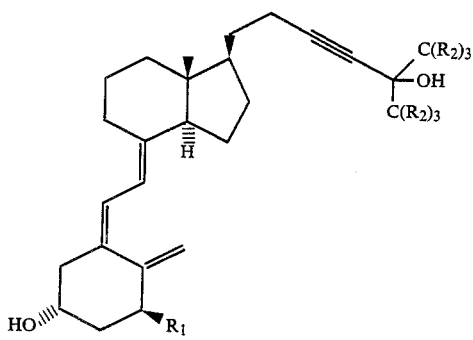

wherein $R_1$ is hydrogen or hydroxy and $R_2$ is hydrogen or fluorine.

The invention also relates to pharmaceutical compositions comprising a compound of formula I.

The compounds of formula I are useful as agents in the treatment of disease states characterized by metabolic calcium deficiencies. Exemplary of such disease states are osteoporosis and renal osteodystrophy.

DETAILED DESCRIPTION OF THE INVENTION

As used throughout the specification and the appended claims, the term "lower alkyl" denotes a monovalent substituent consisting solely of carbon and hydrogen of from 1 to 8 carbon atoms which may be straight- or branched-chain. Examples of lower alkyl groups are methyl, ethyl, n-propyl, 1-propyl, tert-butyl, hexyl, heptyl, octyl and the like. The term "aryl" denotes an organic radical derived from an aromatic hydrocarbon by the removal of a hydrogen atom. Exemplary of aryl are phenyl and substituted phenyl. The term "substituted" as applied to "phenyl" refers to phenyl which is substituted with one or more of the following groups: lower alkyl, fluorine, chlorine, bromine, iodine, nitro, cyano, trifluoromethyl and the like. The term "aryl-lower alkyl" denotes a lower alkyl as defined above which is substituted by aryl as defined above. The term "protecting or derivatizing group" denotes a chemical moiety conventionally employed to protect hydroxy groups. Exemplary of such protecting groups are —(CO)-lower alkyl and tri-lower alkylsilyl.

In the formulas herein, the various substituents are illustrated as joined to the nucleus by one of the following notations. A dark line (▬▬) indicates that a substituent is in the β-orientation, (that is, above the plane of the molecule), a broken line (⦀⦀⦀) indicates that a substituent is in the α-orientation (that is, below the plane of the molecule), and a wavy line (∼∼) indicates that a substituent may be in either the α or β orientation or a mixture of compounds containing substituents in the α and/or β orientation.

The invention is directed to a compound of the formula

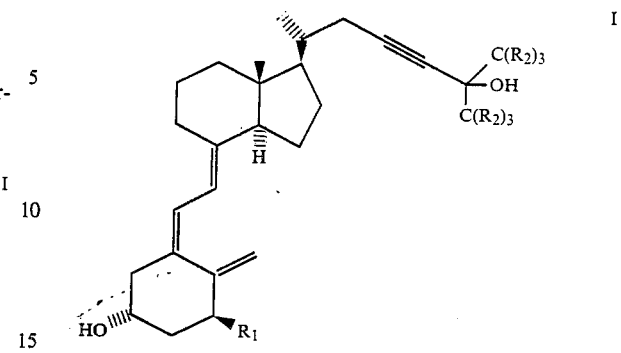

wherein $R_1$ is hydrogen or hydroxy and $R_2$ is hydrogen or fluorine.

Especially preferred among compounds of formula I are those wherein $R_2$ is fluorine.

The invention also relates to pharmaceutical compositions comprising a compound of formula I.

The compounds of formula I are useful as agents in the treatment of disease states characterized by metabolic calcium deficiencies. Exemplary of such disease states are osteoporosis and renal osteodystrophy.

The invention also relates to processes for preparing compounds of formula I.

Compounds of formula I are:
1α,25-dihydroxy-23-yne-cholecalciferol;
25-hydroxy-23-yne-cholecalciferol;
1α,25-dihydroxy-23-yne-26,26,26,27,27,27-hexafluoro-cholecalciferol; and
25-hydroxy-23-yne-26,26,26,27,27,27-hexafluoro-cholecalciferol.

The compounds of formula I can be prepared as described below.

In the description of the preparation of compounds of formula I, reference is made to Formula Schemes 1, 2, and 3.

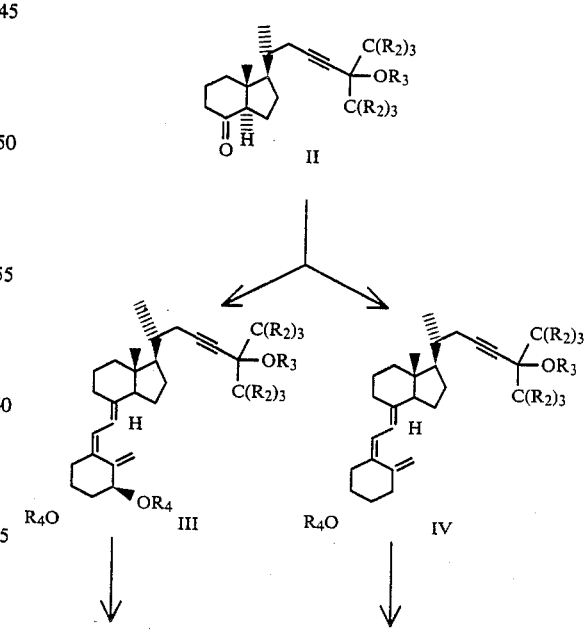

Formula Scheme 1

-continued
Formula Scheme 1

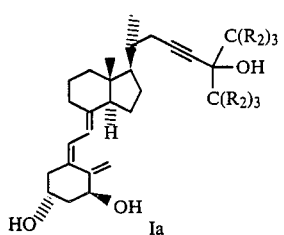 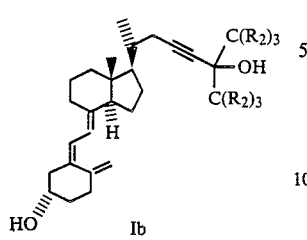

wherein R$_2$ is hydrogen or fluorine, R$_3$ and R$_4$ are —Si(R$_5$)$_3$ wherein R$_5$ is lower alkyl, aryl or aryl-lower alkyl.

In accordance with Formula Scheme 1 a compound of formula II can be reacted with a compound of formula

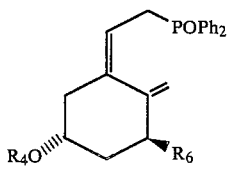 V wherein R$_6$ is hydrogen or OR$_4$, R$_4$ is as described above
to obtain a corresponding compound of formula III or IV.

The compounds of formula V are known or can be prepared in accordance with known procedures. (See e.g. E. G. Baggiolini, J. A. Iacobelli, B. M. Hennessy, A. D. Batcho, J. F. Sereno, M. R. Uskokovic, J. Org. Chem. 1986, (51), 3098.).

The reaction is carried out in the presence of a strong base in a conventional ether solvent under an inert atmosphere and at a temperature in the range of from about −80° C. to about −50° C. Exemplary of suitable bases are alkyl lithium compounds and dialkyl or alkyl substituted disilyl amides. Compounds of formulas III or IV can be purified by elution chromatography on silica gel.

The compounds of formulas III or IV are then converted to the corresponding cholecalciferol derivatives of formulas Ia or Ib by removal of the hydroxyl derivatizing groups. This can be achieved most preferably by treatment of a compound of formula III or IV with organic fluoride salts like tetrabutylammonium fluoride at room temperature and a suitable solvent preferably tetrahydrofuran.

Alternatively, the deprotection especially of compounds of formula III can be carried out by treatment of a compound of formula III or IV with a lower alkanol or with mixtures of water and a miscible organic solvent in the presence of an acid. While any mineral acid or lower alkanoic or sulfonic acid may be used it is preferred to use the hydrogen form of a cationic exchange resin (for example, AG50W-X4 Bio-Rad Laboratories, Amberlite CG120, Rohm and Haas Co. Amerlyst 15 Rohm and Haas Company, Dowex 50X4 Dow Chemical Company) as a suspension in a lower alkyl alcohol.

As can be seen, compounds of formulas Ia and Ib are encompassed by formula I.

A compound of formula II, wherein R$_2$ is hydrogen, can be prepared as described below with particular reference to Formula Scheme 2 below.

Formula Scheme 2

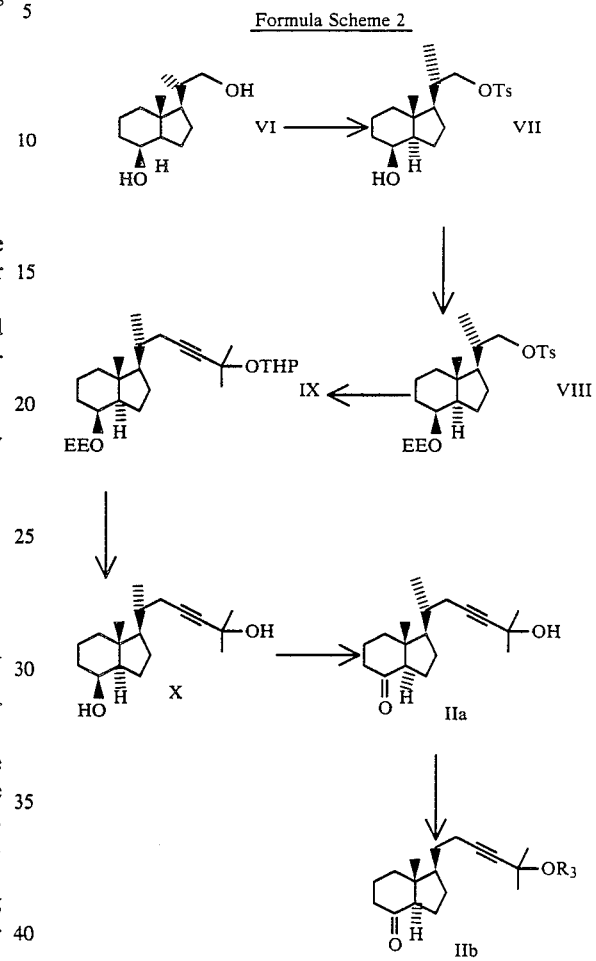

wherein Ts is tosyl, OTHP is tetrahydropyranyloxy, EEO is ethoxyethoxy and R$_3$ is as described above.

In accordance with Formula Scheme 2, the compound of formula VI, which is known, (See e.g. P. M. Wovkulich, F. Barcelos, A. D. Batcho, J. F. Sereno, E. G. Baggiolini, B. M. Hennessy and M. R. Uskokovic, Tetrahedron 40, 2283 (1984)) is converted to the compound of formula VII with a conventional tosylating agent such as p-toluenesulfonyl chloride in a basic solvent such as collidine, or more preferably, pyridine, at about −10° C. to about 10° C., preferably 0° C., for about 2 hours to about 10 hours, under an inert atmosphere, such as nitrogen.

The compound of formula VII is converted to the compound of formula VIII by reaction with ethyl vinyl ether in an aprotic solvent and in the presence of an acid, at about −90° C. to about −60° C., preferably −70° C., under an inert atmosphere such as nitrogen. The acid can be benzoic acid, or more preferably p-toluenesulfonic acid.

The compound of formula VIII is then converted to the compound of formula IX. This is done by stirring a mixture of the lithium derivative of the tetrahydropyranylether of 3-methyl-1-butyn-3-ol, (preferably using an alkyllithium such as n-butyllithium, and dry dioxane, under an inert atmosphere, such as argon, at a temperature of 0° to 5° C.) with the compound of formula VIII and heating to reflux for about 20 to about 80 hours. All these operations are conducted under an inert atmosphere. The compound of formula IX is obtained following a conventional work-up.

The compound of formula IX is then converted to the compound of formula X by reaction with an acid, such as p-toluenesulfonic acid initially in a lower alkanol, such as methanol, at about −10° C., preferably 0° C., and then at about room temperature. The compound of formula X is obtained after a conventional work-up.

The compound of formula X is then oxidized to give the compound of formula IIa by reaction with an oxidating agent such as pyridinium chlorochromate in a lower alkyl halide solvent such as chloroform, carbon tetrachloride, or more preferably dichloromethane, at a temperature in a range of about −10° C. to about 30° C. with room temperature being especially preferred.

The ketone of formula IIa may be used directly as a starting material of formula II in Formula Scheme I. It is, however, better to convert the ketone of formula IIa to the ketone of formula IIb which can also be used as a starting material of formula II in Formula Scheme 1. As can be seen, the compounds of formulas IIa and IIb are encompassed by formula II.

The ketone of formula IIa is converted to the ketone of formula IIb by treatment with a silylating agent such as

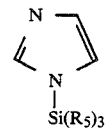

wherein $R_5$ is as described above in an inert organic solvent such as an ether or a halogenated hydrocarbon like dichloromethane, under an inert atmosphere such as argon. A preferred silylating agent is trimethylsilylimidazole.

A compound of formula II, wherein $R_2$ is fluorine, can be prepared as described below with particular reference to Formula Scheme 3 below.

Formula Scheme 3

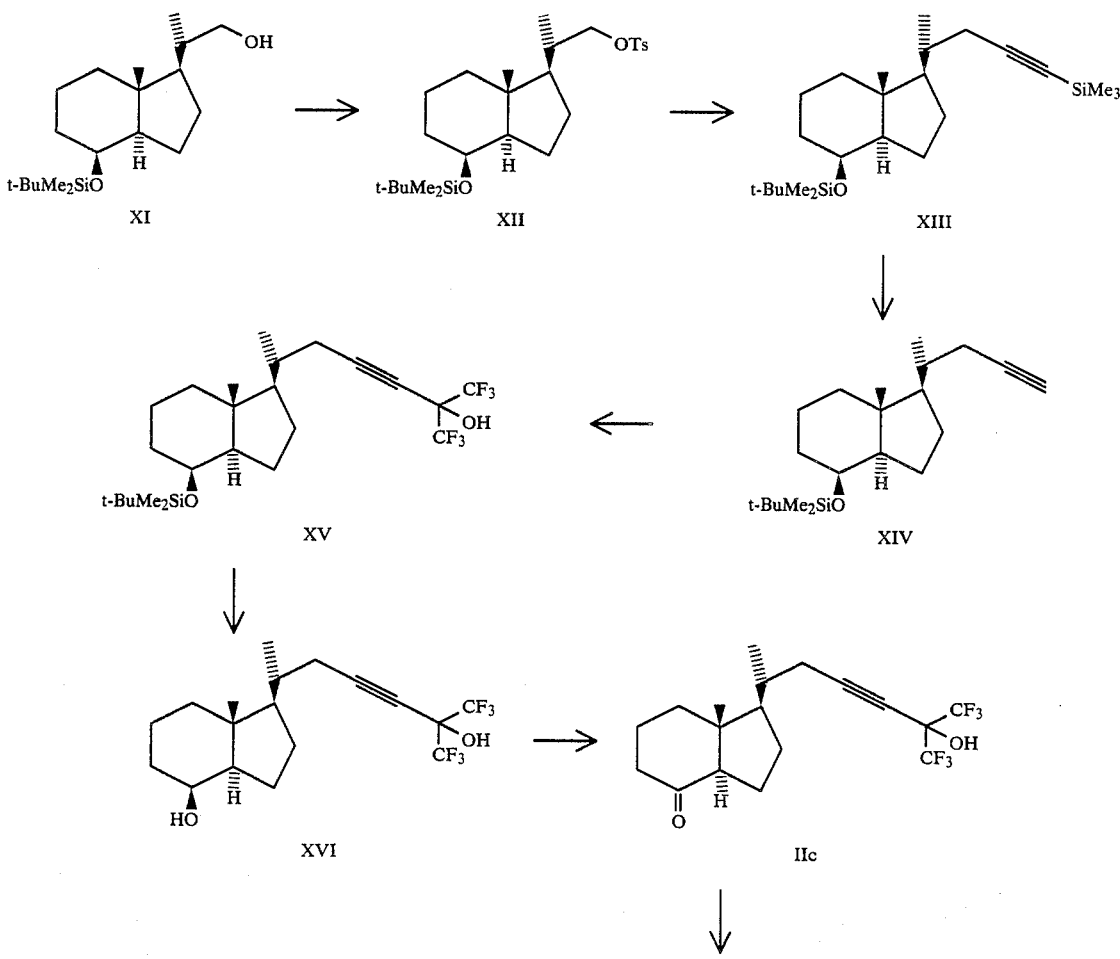

-continued
Formula Scheme 3

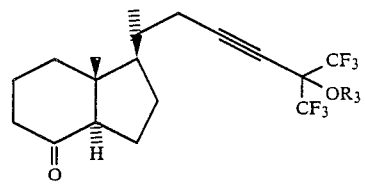

IId wherein R₃ is as described above.

In accordance with Formula Scheme 3, the compound of formula XI, which is known or can be prepared in accordance with known methods is converted to the compound of formula XII with a conventional tosylating agent such as p-toluenesulfonyl chloride in a basic solvent such as collidine, or more preferably pyridine, at about −10° C. to about 10° C., preferably 0° C., for about 10 to about 40 hours under an inert atmosphere such as argon.

The compound of formula XII is converted to the compound of formula XIII. This is done by reacting the n-butyl lithium derivative of (trimethylsilyl)acetylene and prepared with n-butyllithium in dry dioxane at about 0° C. to about 10° C., with the compound of formula XII. The resulting mixture is heated at reflux for 20 to 40 hours. The compound of formula XIII is obtained upon conventional work-up.

The compound of formula XIII is converted to the compound of formula XIV by reaction with silver nitrate followed by potassium cyanide in an aqueous alkanolic solvent such as ethanol and water. The compound of formula XIV is obtained following a conventional work-up.

The compound of formula XIV is converted to the compound of formula XV by reaction with hexafluoroacetone gas in the presence of an alkyllithium such as n-butyllithium. The reaction is carried out in a conventional ether solvent, such as dry tetrahydrofuran, at −90° C. to about −70° C., preferably −75° C. The compound of formula XV is obtained after a conventional work-up.

The compound of formula XV is converted to the compound of formula XVI by reaction with hydrofluoric acid in acetonitrile and dry tetrahydrofuran. The compound of formula XVI is obtained after a conventional work-up.

The compound of formula XVI is oxidized to obtain the compound of formula IIc by reaction with an oxidating agent such as 2′,2′-bipyridinium chlorochromate in a lower alkyl halide solvent such as chloroform, carbon tetrachloride, or more preferably dichloromethane in the presence of anhydrous sodium acetate at about 10° C. to about 40° C., preferably room temperature.

The compound of formula IIc may be used directly as a starting material of formula II in Formula Scheme 1. It is better, however, to use the compound of formula IId which can be obtained from the compound of formula IIc as the starting material of formula II in Formula Scheme 1. As can be seen, the compounds of formulas IIc and IId are encompassed by formula II.

The compound of formula IIc is converted to the compound of formula IId by treatment with a silylating agent such as

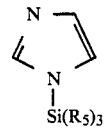

wherein R₅ is as described above in an inert organic solvent such as an ether or a halogenated hydrocarbon like dichloromethane, under an inert atmosphere such as argon. A preferred silylating agent is trimethylsilylimidazole.

As can be seen, compounds of formulas Ia and Ib are encompassed by formula I.

The compounds of formula I can be administered in dosages that are in the range of about 0.25 $\mu$g to about 2 $\mu$g per day to warm-blooded animals in need thereof for the treatment of disease states characterized by metabolic calcium deficiencies such as renal osteodystrophy, and especially, osteoporosis.

The compounds of formula I can be administered orally, subcutaneously, intramuscularly, intravenously or intraperitoneally in the treatment of disease states characterized by metabolic calcium deficiencies such as osteoporosis and renal osteodystrophy.

The useful activity of compounds of formula I can be demonstrated utilizing, for instance, the test procedures which follow.

Stimulation of Intestinal Calcium Absorption and Bone Calcium Mobilization in Rat Experimental Procedures:

Male weanling rats (Holtzman, Madison WI.) were housed individually in overhanging wire cages and were fed a vitamin D-deficient diet containing low calcium (0.005%) and normal phosphorus (0.3%). Test compounds were dissolved in 10–20 $\mu$l of ethanol. Plasma (1.8 ml), collected from vitamin D, deficient rats was added to the ethanol solution. The test compounds were given intrajugularly in 0.3 ml of the ethanol-plasma carrier solution. Controls received carrier alone.

Eighteen hours after injection, the rats were decapitated and their duodena were used to measure intestinal ⁴⁵Ca transport (ICA) by the everted gut sac technique. The duodena were prepared by dissecting free the first 10 cm of the intestine distal to the pyloric valve. The tissue was immediately rinsed with cold 0.9% saline. After rinsing, as much mesentery that could be removed was trimmed free and the intestine everted in a manner such that the distal end remained tied to the everting rod. The intestine was ligated just distal to the pyloric valve. It was then cut to a length of 5.5 cm, and filled with 0.6 ml of incubation buffer. The sac was tied off and placed in a 25 ml flask containing 10 ml of incubation buffer and incubated at 37° C. for 90 minutes. The flask was continuously gassed with 95/5 $O_2/CO_2$. At termination of the experiment the contents of the sac were drained into a test tube and a portion was counted for $^{45}Ca$ presence. An aliquot of the buffer from the incubation flask was also counted for radioactive $^{45}Ca$. Data were expressed as the ratio (S/M) of the tracer concentration in the serosal (S) media (inside the sac) to the concentration of the tracer in the mucosal (M) media (outside the sac).

Bone Ca resorption (BCR) was estimated by measuring the blood Ca increase in the treated rats. Blood was collected in heparinized tubes and centrifuged. The resulting plasma was measured for calcium concentration by atomic absorption spectroscopy. Since rats were fed a diet essentially devoid of Ca, plasma Ca increases reflected mobilization of Ca from bone, not intestinal Ca absorption.

All data (intestinal and bone) were expressed relative to 1,25-$(OH)_2D_3$ using the following formula:

$$\text{Response (ICA or BCM)} = \frac{x - z}{y - z} \times 100$$

where x is the response elicited by the test compound, y is the response elicited with 1,25-$(OH)_2D_3$, and z is the response in the control animals.

Competitive Binding to 1,25-$(OH)_2D_3$ Intestine Receptors

Experimental Procedures

The ability of vitamin $D_3$ metabolites to compete for 1,25-$(OH)[^3H]D_3$ receptor binding sites was evaluated with receptor prepared from intestine of chick, rat and calf. The receptor was prepared by removing 10–12% of the small intestine immediately adjacent to the pyloric spincter which was washed immediately with cold buffer containing 500 mM KCl, 50 mM Tris, 1.5 mM EDTA, and 5 mM dithiothreitol, pH 7.4 (KTED buffer). Mucosa was collected and washed three times with 10 volumes of cold KTED buffer. The washed mucosa was homogenized in KTED buffer (20% w/v) using a Polytron Pt20 tissue disruptor. Cytosol was prepared by centrifugation of the homogenized mucosa at 300,000×g for 1 hour. Receptor was precipitated from the cytosol by the addition of ammonium sulphate to achieve 35% saturation. The ammonium sulphate treated cytosol was centrifuged at 20,000×g for 10 minutes. The supernatant was discarded and the pellet lyophilized and stored at 31 70° C. Prior to binding assay the pellet was resuspended in cold binding assay buffer containing 150 mM KCl, 50 mM $NaPO_4$, 1.5 mM EDTA and 5 mM dithiothreitol. The receptor was prepared in such a manner that 50% of the 1,25-$(OH)_2[^3H]D_3$ was specifically bound in the presence of 200 pM (40 pg/tube) non-radioactive 1,25-$(OH)_2D_3$. Results of test compounds were related to 1,25-$(OH)_2D_3$ using the following formula:

$$a/b \times 100$$

where a is the quantity of 1,25-$(OH)_2D_3$ that will displace 50% of the 1,25-$(OH)_2[^3H]D_3$ and b is the amount of test compound that will displace 50% of the 1,25-$(OH)_2[^3H]D_3$.

Results of the above tests are contained in Table I below.

TABLE I

| | | % of 1,25-$(OH)_2D_3$ Effect in Rat | | Competitive Binding to 1,25-$(OH)_2D_3$ Receptors - % of 1,25-$(OH)_2D_3$ Effect | | |
| --- | --- | --- | --- | --- | --- | --- |
| | | INTESTINAL | | | | |
| Compound | CONCENTRATION NG/RAT | CALCIUM ABSORPTION | BONE CALCIUM MOBILIZATION | RAT INTESTINE | CHICK INTESTINE | CALF INTESTINE |
| 1,25-$(OH)_2D_3$ | 12.5 | 100 | 100 | 100 | 100 | 100 |
| 1,25-$(OH)_2$—23-yneD$_3$ | 15.5 | 95 | 15 | 39 | 60 | 47 |
| 25-(OH)—23-yneD$_3$ | 12.5 | 71 | 0 | | 0 | 0 |
| 1,25-$(OH)_2$—23-yne-26,27F$_6$—D$_3$ | 12.5 | 124 | 0 | 142 | 47 | 62 |
| 25-(OH)—23-yne-26,27F$_6$—D$_3$ | 12.5 | 0 | 11 | | 0 | 0 |

Data from Table I indicate that in comparison to 1,25-dihydroxycholecalciferol the corresponding analogs bearing the C-23 triple bond generally exhibit greater intestinal calcium absorption than bone calcium mobilization activities. These analogs bind to intestinal 1,25-$(OH)_2D_3$ receptors.

Evaluation of 1α,25-Dihydroxycholecalciferol and of 1α,25-Dihydroxy-23-yne-26,26,26,27,27,27-hexafluorocholecalciferol in Vitamin D Deficient Rats Experimental Procedures Rats were placed on the following protocol.

D+ Control: Ten 3 week old rats were maintained on vitamin $D_3$ replete diet for 6 weeks.

D− Control: Ten 3 week old rats were maintained on vitamin $D_3$ deficient diet for 6 weeks.

Low Dose Treatment: One hundred 3 week old rats were maintained for 3 weeks on vitamin $D_3$ deficient diet, and the following 3 weeks treated with a low dose (See Table III) of 1,25-$(OH)_2D_3$ or 1,25-$(OH)_2$-23-yne-26,27F$_6$D$_3$, while maintaining the same diet.

High Dose Treatment: One hundred 3 week old rats were maintained for 3 weeks on vitamin $D_3$ deficient diet, and the following 3 weeks treated with a high dose (See Table III) of 1,25-$(OH)_2D_3$ or 1,25-$(OH)_2$-23-yne-26,27F$_6$D$_3$, while maintaining the same diet.

The following parameters in Table II were evaluated, by means which are conventional in the art, after completion of the above treatments. Bone mass is measured by known histomorphormetric methods.

TABLE II

| | Daily Dose ng | Body Weight gr | Serum $Ca^{2+}$ mg/dl | Serum $PO_4^{2-}$ mg/dl | Serum Creatinine mg/dl | Bone Mass mm$^3$/cm$^3$ |
| --- | --- | --- | --- | --- | --- | --- |
| 1,25-$(OH)_2D_3$ | 15 | 192 ± 4.5 | 11.76 ± 0.16 | 7.61 ± 0.31 | 0.37 ± 0.04 | 156 ± 16 |
| | 60 | 156 ± 15 | 11.92 ± 0.40 | 6.58 ± 0.30 | 0.35 ± 0.02 | 296 ± 56 |

TABLE II-continued

| | Daily Dose ng | Body Weight gr | Serum $Ca^{2+}$ mg/dl | Serum $PO_4^{2-}$ mg/dl | Serum Creatinine mg/dl | Bone Mass $mm^3/cm^3$ |
|---|---|---|---|---|---|---|
| 1,25-(OH)$_2$—23-yne-26,27F$_6$—D$_3$ | 18 | 148 ± 4.3 | 15.63 ± 0.36 | 7.66 + 0.17 | 0.60 ± 0.05 | 385 ± 77 |
| | 72 | 111 ± 5.9 | 15.23 ± 0.22 | 6.34 + 0.26 | 0.43 ± 0.06 | 746 + 48 |
| D− control | | 184 ± 1.3 | 5.60 ± 0.5 | 8.65 ± 0.6 | 0.44 ± 0.04 | 96.5 + 9 |
| D+ control | | 202 ± 3.1 | 10.41 ± 0.10 | 5.76 + 0.12 | 0.41 ± 0.01 | 168 + 15 |

As used herein 1,25-(OH)$_2$D$_3$ is 1α,25-dihydroxycholecalciferol;

1,25-(OH)$_2$-23-yne-D$_3$ is 1α,25-dihydroxy-23-yne-cholecalciferol;

25-(OH)-23-yne D$_3$ is 25-hydroxy-23-yne-cholecalciferol;

1,25-(OH)$_2$-23-yne-26,27F$_6$-D$_3$ is 1α,25-dihydroxy-23-yne-26,26,26,27,27,27-hexafluorocholecalciferol.

1,25-(OH)-23-yne-26,27F$_6$-D$_3$ is 25-hydroxy-23-yne-26,26,26,27,27,27-hexafluorocholecalciferol.

Inhibition of Cell Proliferation and Induction of Cell Differentiation

Cultures of HL-60 promyelocytic leukemia cells were established in the absence (control) and presence of various concentrations of test compounds. After an 8-day incubation period, the cultures were evaluated for proliferation of tumor cells, cell viability, and cellular differentiation. Proliferation was assessed by directly enumerating the increased number of tumor cells resulting from cell division during incubation. Viability was assessed by dye exclusion technique to learn whether any of the compounds were lethal to the cultured HL-60 cells. Cellular differentiation was evaluated by determining the number of cells which had acquired the enzymes necessary to support a respiratory burst, a characteristic of mature macrophages and granulocytes.

METHODS

Tissue culture medium used in these experiments was RPMI-1640 supplemented to 10% v/v with heat-inactivated fetal bovine serum and to an additional 1.6 mM with L-glutamine.

Test compounds were dissolved in sufficient ethanol to yield stock solutions of $1 \times 10^{-2}$ or $1 \times 10^{-3}$ molar. Reduced lighting was used when working with compounds and stock solutions were stored in the dark at −20° C. in an argon atmosphere. Compounds were diluted in tissue culture medium and added to flasks containing HL-60 cells to achieve the final concentration described in each test.

The HL-60 tumor cell line was originally derived from a patient with promyelocytic leukemia and was obtained from the American Type Culture Collection. The cells were maintained in liquid culture by serial passage twice weekly in tissue culture medium. Cells were routinely tested for mycoplasma and were found to be negative. In any test, three replicate flasks were incubated without compound (control) or in the presence of varying concentrations of test compound. Ethanol, used as the vehicle, was kept constant in all dilutions in each test and had no effect on cell proliferation, viability or cell differentiation at the concentrations used (≦0.1%). After 8 days of incubation at 37° in a humidified atmosphere of 5% $CO_2$ in air, cultures were evaluated for tumor cell proliferation, viability and differentiation.

Quantitation of proliferation was done by enumerating the number of HL-60 cells in each individual flask (3 flasks per experimental point) using an Elzone electronic particle counter. Results are shown as the percent reduction of cell number calculated for each concentration tested according to the formula:

$$\left(1 - \frac{\text{mean number of cells in experimental cultures}}{\text{mean number of cells in control cultures}}\right) \times 100$$

The results are also expressed as the concentration which reduced the cell number by 50% ($ID_{50}$).

Viability of tumor cells was determined by the method of trypan blue dye exclusion. Cells in tissue culture medium were added to an equal volume of 0.4% trypan blue in saline. Cells were scored as viable upon microscopic examination if they excluded dye and as dead if they were stained blue. The viability of cells from test cultures were not appreciably different from control cultures, except occasionally at the highest concentrations tested, indicating that the compounds tested were not toxic to HL-60 cells at concentrations which inhibited proliferation and induced cellular differentiation.

Quantitation of differentiated cells was done by the biochemical method of nitroblue tetrazolum (NBT) reduction. One million HL-60 cells were pooled from replicate cultures, centrifuged at 220×g for 10 minutes, and resuspended in 1 ml of $Ca^{++}$-$Mg^{++}$-deficient phosphate buffered saline prepared by supplementing $Ca^{++}$-$Mg^{++}$-free phosphate buffered saline (PBS) to 20% v/v with heat-inactivated fetal bovine serum). Nitroblue tetrazolium was dissolved at 0.5 mg per ml in $Ca^{++}$-$Mg^{++}$-free PBS with gentle heating and frequent mixing. A stock solution of 1 mg tetradecanoyl phorbol acetate (TPA) per ml in ethanol, stored at −20°, was diluted 100-fold with $Ca^{++}$-$Mg^{++}$-free PBS to prepare a working solution. The test was done by adding 1 ml of NBT solution and 0.02 ml of the working TPA solution to the HL-60 cells. After mixing, the tubes were incubated in a 37° water bath for 25 minutes then transferred to ice. Undifferentiated and differentiated cells present in any sample were determined microscopically by surveying a minimum of 300 cells per sample. Cells without pigmented granules (clear cells) were judged to be undifferentiated while those containing greater than 3 blue-black formazan granules were scored as differentiated. Generally, differentiated cells were intensely pigmented clearly indicating the enzymatic conversion of NBT to formazan. Results are expressed as the percentage of differentiated cells present in any sample as calculated according to the formula:

$$100 \times \frac{\text{number of formazan positive cells}}{\text{total number of cells counted}}$$

The results are also expressed as the concentration of compound which induced differentiation of 50% of the cells ($ED_{50}$).

RESULTS

The results of these tests are shown in Table 1 and document that each of the compounds tested inhibited the proliferation of HL-60 tumor cells. The anti-proliferative effect of each compound was also dose-dependent and the dose response curves were used to obtain the $ID_{50}$ values shown. Cellular differentiation was also clearly stimulated in a dose-dependent manner by each of the compounds tested.

Again, the dose response curves were employed to determine the $ED_{50}$ values shown in Table 1. There was no impact of the vehicle on cellular proliferation, viability or differentiation.

The data indicate that each of the compounds in question restrained the proliferation of human promyelocytic cells, in vitro. Furthermore, the cells were seen to differentiate toward a more mature phenotype at the same doses which inhibited proliferation.

TABLE 3

Anti-proliferative and Differentiation-inducing Effects of Compounds of Formula I on HL-60 Tumor Cells.

| Compound | Conc. ($\times 10^{-8}$ M) | % Reduction in cell number | $ID_{50}$ ($\times 10^{-8}$ M) | % Differentiated cells | $ED_{50}$ ($\times 10^{-8}$ M) |
|---|---|---|---|---|---|
| A | 0.01 | Not Done | | Not Done | |
| | 0.1 | 30 | | 15 | |
| | 1 | 67 | 0.6 | 54 | 0.9 |
| | 10 | 85 | | 98 | |
| B | 0.01 | 15 | | 13 | |
| | 0.1 | 31 | | 29 | |
| | 1 | 85 | 0.2 | 95 | 0.2 |
| | 10 | 89 | | 98 | |
| C | 1 | Not Done | | Not Done | |
| | 10 | 0 | | 5 | |
| | 100 | 31 | 150 | 27 | 150 |
| | 300 | 79 | | 95 | |
| D | 1 | 0 | | 6 | |
| | 10 | 14 | 25 | 27 | 20 |
| | 100 | 77 | | 99 | |

In the above table,

Compound A is 1α,25-dihydroxy-23-yne-cholecalciferol;

Compound B is 1α,25-dihydroxy-23-yne-26,26,26,27,27,27-hexafluorocholecalciferol;

Compound C is 25-hydroxy-23-yne-cholecalciferol; and

Compound D is 25-hydroxy-23-yne-26,26,26,27,27,27-hexafluorocholecalciferol.

The above test procedures show that compounds of formula I inhibit cell proliferation and induce cell differentiation. According, the compounds of formula I are useful as agents in the treatment of neoplastic diseases such as leukemia.

The compounds of formula I can be formulated in compositions such as tablets, capsules and the like, or elixirs for oral administration, or in sterile solutions or suspensions for parenteral administration, or in topical formulations. About 0.25 to about 2 μg of a compound of formula I can be compounded with a pharmaceutically acceptable vehicle, carrier, excipient, binder, preservative, stabilizer, flavor and the like, in a unit dosage as called for by accepted pharmaceutical practice. The amount of active substance in the foregoing compositions or preparations is in the range previously indicated.

Illustrative of the adjuvants which may be incorporated into capsules, and the like are the following: a binder such as gum tragacanth, acacia, corn starch, or gelatin; an excipient such as dicalcium phosphate; a disintegrating agent such as corn starch, potato starch, algenic acid and the like; a lubricant such as magnesium stearate a sweetening agent such as sucrose, lactose or saccharin; a flavoring agent such as peppermint, oil of wintergreen or cherry. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle, such as water for injection, a naturally occurring vegetable oil, such as sesame oil, coconut oil, peanut oil, cottonseed oil, and the like, or a synthetic fatty vehicle such as ethyl oleate or the like. Buffers, preservatives, anti-oxidants and the like can be incorporated as required.

Compositions for topical administration can be prepared by conventional means, and, in particular, as illustrated in examples given below.

The examples which follow further illustrate the disclosure. All temperatures are in degrees Celsius unless otherwise stated.

EXAMPLE 1

A mixture of 2.12 g (0.010 mole) of [1R-[1α,3aβ,4α,7aα]]-octahydro-4-hydroxy-β,7a-dimethyl-1H-indene-1-ethanol [H. T. Toh and W. H., Okamura, J. Org. Chem., 48, 1414 (1983)], 2.10 g of p-toluenesulfonyl chloride and 9 mL of dry pyridine was stirred at 0° C. for 3 hours under nitrogen. The reaction mixture was poured into ice water and extracted with methylene chloride. The organic layer was consecutively washed with water, 1N sulfuric acid, and saturated aqueous sodium bicarbonate solution. The solution was dried over anhydrous magnesium sulfate, filtered and evaporated to dryness to yield 3.70 g of [1R-[1α,3aβ,4α,7aα]]-octahydro-4-hydroxy-β,7a-dimethyl-1H-indene-1-ethanol α-(4-methylbenzenesulfonate). An analytical sample was prepared by recrystallization from methanol, m.p. 97°-98°; $[\alpha]_D^{25}+23°$ (c 0.5, CHCl$_3$).

EXAMPLE 2

A mixture of 3.68 g (0.010 mole) of [1R-[1α,3aβ,4α,7aα]]-octahydro-4-hydroxy-β,7a-dimethyl-1H-indene-1-ethanol α-(4-methylbenzenesulfonate), 100 mL of ethyl vinyl ether and 0.04 g of p-toluenesulfonic acid monohydrate was stirred at −70° for 1 hour under nitrogen and allowed to warm to 0° for 0.5 hours. The mixture was quenched with 2 mL of triethylamine and evaporated to dryness under vacuum. The residue was dissolved in methylene chloride which was washed with saturated aqueous sodium bicarbonate. The organic phase was dried over anhydrous magnesium sulfate, filtered, and evaporated to dryness to yield 4.60 g of [1R-[1α,3aβ,4α,7aα]]-4-(1-ethoxyethoxy)octahydro-β,7a-dimethyl-1H-indene-1-ethanol 4-methylbenzenesulfonate as an oil, $[\alpha]_D^{25}+31°$ (c 1.2, CHCl$_3$).

EXAMPLE 3

A mixture of 1.26 g (0.0075 mole) of the tetrahydropyranyl ether of 3-methyl-1-butyn-3-ol and 5.0 mL (0.0075 mole) of 1.5M n-butyllithium in hexane and 30 mL of dry dioxane were stirred at 5° for 0.5 hour and at room temperature for 1 hour under an argon atmosphere. Then, 1.32 g (0.0030 mole) of [1R-[1α,3aβ,4α,7aα]]-4-(1-ethoxyethoxy)octahydro-β,7a-dimethyl-1H-indene-1-ethanol 4-methylbenzenesulfonate was added and the mixture was heated at reflux for 36 hours and cooled. The mixture was poured into water and extracted with ethyl acetate. The organic layer was washed with water and brine, and was dried over anhydrous magnesium sulfate. The mixture was filtered and evaporated to dryness under a high vacuum to remove all volatile material. The residue was purified by column chromatography on silica gel using 4:1 hexane-ethyl acetate as eluent to yield 1.43 g of [1R-[1α,3aβ,4α,7aα]]-2-[[5-[4-(1-ethoxyethoxy)-octahydro-7a-methyl-1H-inden-1-yl]-1,1,5-trimethyl-2-pentynyl]oxy]-tetrahydro-2H-pyran as an oil, $[\alpha]_D^{25}+36°$ (c 1.0, CHCl$_3$).

EXAMPLE 4

A mixture of 3.50 g (about 0.0073 mole) of crude [1R-[1α,3aβ,4α,7aα]]-2-[[5-[4-(1-ethoxyethoxy)octahydro-7a-methyl-1H-inden-1-yl]-1,1,5-trimethyl-3-pentynyl]oxy]-tetrahydro-2H-pyran, 50 mL of methanol and 0.10 g of p-toluenesulfonic acid monohydrate was stirred at 0° C. for 0.5 hours and at 23° C. for 18 hours under nitrogen. The mixture was then concentrated under reduced pressure to about 10 mL. The mixture was diluted with methylene chloride and washed with saturated aqueous sodium bicarbonate solution. The combined aqueous phases were then back-extracted with methylene chloride. The combined organic phases were dried over anhydrous magnesium sulfate, filtered, and evaporated to dryness under vacuum to yield 2.65 g of crude product. The crude product was purified by column chromatography on silica gel using 5:1 hexane-ethyl acetate as eluent to yield 1.84 g of [1R-[1α,3aβ,4α,7aα]]-octahydro-1-(5-hydroxy-1,5,5-trimethyl-3-pentynyl)-7a-methyl-1H-inden-4-ol. An analytical sample was prepared by recrystallization from ether-hexane, m.p. 62°-63°; $[\alpha]_D^{22}+39°$ (c 1.0, CHCl$_3$).

EXAMPLE 5

To a suspension of 2.40 g (0.011 mole) of pyridinium chlorochromate in 50 mL of methylene chloride at 0° C. was added 0.60 g (0.0022 mole) of [1R-[1α,3aβ,4α,7aα]]-octahydro-1-(5-hydroxy-1,5,5-trimethyl-3-pentynyl)-7a-methyl-1H-inden-4-ol in 10 mL of methylene chloride and the mixture was stirred at 0° C. for 0.5 hours and at 23° C. for 1 hour under nitrogen. The mixture was diluted with ether and stirred for 10 minutes. The heterogeneous mixture was filtered through a ¼" bed of diatomaceous earth and the bed was washed with ether. The combined filtrates were evaporated to dryness under vacuum to yield 0.87 g of a dark oil. This material was suspended in ether and filtered through a ¼" bed of diatomaceous earth. Again the bed was washed with ether. The combined filtrates were evaporated to dryness to yield 0.45 g of a yellow oil. The crude product was purified by column chromatography on silica gel using 6:1 hexane-ethyl acetate as eluent to give 0.41 g of [1R-[1α,3aβ,7aα]]-octahydro-1-(5-hydroxy-1,5,5-trimethyl-3-pentynyl)-7a-methyl-4H-inden-4-one.

EXAMPLE 6

A mixture of 0.18 g (0.00065 mole) of [1R-[1α,3aβ,7aα]]-octahydro-1-(5-hydroxy-1,5,5-trimethyl-3-pentynyl)-7a-methyl-4H-inden-4-one, 1.80 g (0.013 mole) of trimethylsilylimidazole and 5 mL of dry methylene chloride was stirred at 25° for 18 hours under an argon atmosphere. The solution was quenched by adding 1 g of ice and stirring the heterogeneous mixture for 10 minutes. The mixture was then poured into ice water and extracted with methylene chloride. The combined organic phases were washed with water, dried over anhydrous magnesium sulfate, filtered, and evaporated to dryness under vacuum to yield 0.23 g of crude product. This material was purified by column chromatography on silica gel using 6:1 hexane-ethyl acetate as eluent to give 0.21 g of [1R-[1α,3aβ,7aα]]-octahydro-1-[1,5,5-trimethyl-5-[(trimethylsilyl)oxy]-3-pentynyl]-7a-methyl-4H-inden-4-one.

EXAMPLE 7

A mixture of 0.32 g (0.00051 mole) of [3S-(1Z,3α,5β)]-2-[3,5-bis[[(1,1-dimethylethyl)dimethylsilyl]oxy]-2-methylenecyclohexylidene]ethyl]diphenylphosphine oxide [E. G. Baggiolini, J. A. Iacobelli, B. M. Hennessy, and M. R. Uskokonic, J. Amer. Chem. Soc. 104, 2945 (1982)] and 8 mL of dry tetrahydrofuran was cooled to −78° under an argon atmosphere and 0.32 mL (0.00051 mole) of 1.6M n-butyllithium in hexane was added slowly by syringe. A deep red solution formed and was stirred at −78° for 10 minutes. A solution of 0.10 g (0.00029 mole) of [1R-[1α,3aβ,7aα]]octahydro-1-[1,5,5-trimethyl-5-[(trimethylsilyl)oxy]-3-pentynyl]-7a-methyl-4H-inden-4-one in 2 mL of dry tetrahydrofuran was added slowly by syringe and the red solution was stirred at −78° for 1.5 hours. The mixture was quenched by adding 4 mL of a saturated aqueous solution of a 1:1 mixture of 1M potassium sodium tartrate and 2M potassium bicarbonate. The mixture was warmed to 25° and diluted with 30 mL of the saturated aqueous solution of a 1:1 mixture of 1M potassium sodium tartrate and 2M potassium bicarbonate. This solution was extracted with ethyl acetate. The combined organic phases were washed with water followed by brine. The organic phase was dried over anhydrous magnesium sulfate, filtered, and evaporated to dryness under vacuum to yield 0.44 g of crude product. This material was purified by column chromatography on silica gel using 19:1 hexane-ethyl acetate as eluent to give 0.13 g of (1α,3β,5Z,7E)-1,3-bis[[(1,1-dimethylethyl)dimethylsilyl]oxy]-25-[(trimethylsilyl)oxy]-9,10-secocholesta-5,7,10(19)-trien-23-yne as a colorless oil, $[\alpha]_D^{25} +37.8°$ (c, 0.52, CHCl$_3$).

EXAMPLE 8

A mixture of 0.12 g (0.00017 mole) of (1α,3β,5Z,7E)-1,3-bis[[(1,1-dimethylethyl)dimethylsilyl]oxy]-25-[(trimethylsilyl)oxy]-9,10-secocholesta-5,7,10(19)-trien-23-yne and 8 mL of 1% tetra-n-butylammonium fluoride in tetrahydrofuran was stirred at room temperature for 18 hours under an argon atmosphere. The mixture was then diluted with water and extracted with ethyl acetate. The combined organic phases were washed with water followed by brine. The organic phase was dried over anhydrous magnesium sulfate, filtered, and evaporated to dryness under vacuum to yield 0.15 g of crude product. This material was purified by column chromatography on silica gel using 2:1 hexane-ethyl acetate as eluent to give 0.069 g of purified product. A second column chromatography on silica gel using 2:1 hexane-ethyl acetate as eluent then gave 0.048 g of (1α,3β,5Z,7E)-9,10-secocholesta-5,7,10(19)-trien-23-yne-1,3,25-triol as a colorless oil, $[\alpha]_D^{22} +22.8°$ (c 0.21, CHCl$_3$).

EXAMPLE 9

A mixture of 2.00 g (6.12 mmol) of [1R-[1α(S*),3β,4α,7aα]]-β,7a-dimethyl-4-[[(1,1-dimethyl)dimethylsilyl]oxy]octahydro-1H-indene-1-ethanol, 2.92 g (15.3 mmol) of p-toluenesulfonyl chloride and 50 mL of dry pyridine was stirred at 0° C. for 19 hours under argon. The reaction was quenched with ice chips. After dilution with water, the mixture was extracted with methylene chloride. The organic phase was consecutively washed with 1N H$_2$SO$_4$, water, and saturated aqueous NaHCO$_3$. The solution was dried (Na$_2$SO$_4$) and evaporated to dryness. The residue was chromatographed on silica gel (40–63μ) using 1:8 ethyl acetate-hexane to afford 2.81 g (96%) of [1R-[1α(S*),3β,4α,7aα]]-β,7a-dimethyl-4-[[(1,1-dimethylethyl)dimethylsilyl]-oxy]octahydro-1H-indene-1-ethanol 4-methylbenzenesulfonate as a glass: $[\alpha]_D^{25} +34.1°$ (c 0.92, CHCl$_3$).

EXAMPLE 10

To a solution of 4.96 mL (34.4 mmol) of (trimethylsilyl)acetylene (98%) in 34 mL of dry dioxane at +5° C. was added dropwise 22.0 mL (35.2 mmol) of 1.6M butyllithium in hexane. After stirring for 30 minutes at +4° then at 25° C. for 1.5 hours, a solution of 2.81 g (5.84 mmol) of [1R-[1α(S*),3β,4α,7aα]]-β,7a-dimethyl-4-[[(1,1-dimethylethyl)dimethylsilyl]oxy]octahydro-1H-indene-1-ethanol-4-methylbenzenesulfonate in 44 mL of dry dioxane was added dropwise. The mixture was heated at reflux for 20 hours, then quenched with brine at 0° C. The mixture was extracted with ether. The organic phase was washed with brine, dried (Na$_2$SO$_4$) and evaporated to dryness. The residue was chromatographed on silica gel (40–63μ) using hexane to give 2.09 g (88%) of [1R-[1α(R*),3β,4α,7aα]]-4-[[4-(1,1-dimethylethyl)dimethylsilyl]oxy]octahydro-7a-methyl-1H-inden-1-yl]-1-pentynyl]trimethylsilane as an oil: $[\alpha]_D^{25} +46.9°$ (c 0.95, CHCl$_3$).

EXAMPLE 11

To a solution of 2.09 g (5.14 mmol) of [1R-[1α(R*),3β,4α,7aα]]-4-[[4-(1,1-dimethylethyl)dimethylsilyl]oxy]octahydro-7a-methyl-1H-inden-1-yl]-1-pentynyl]trimethylsilane in 11 mL of absolute ethanol was added a solution of 2.31 g (13.6 mmol) of silver nitrate in 20 mL of 3:1 ethanol-water. The mixture was stirred at 50° C. for 30 minutes then cooled to 25° C. Then a solution of 4.28 g (65.1 mmol) of potassium cyanide in 11 mL of water was added and the mixture was stirred at 25° C. for 2 hours. The mixture was diluted with water and extracted with ether. The organic phase was washed with water, dried (MgSO$_4$) and evaporated to dryness. The residue was chromatographed on silica gel (40–63μ) using hexane as eluent to yield 1.63 g (95%) of [1R-[1α(R*),3β,4α,7aα]]-[[octahydro-7a-methyl-1-(1-methyl-3-butynyl)-1H-inden-4-yl]oxy]-(1,1-dimethylethyl)dimethylsilane as an oil: $[\alpha]_D^{25} +53.8°$ (c 0.64, CHCl$_3$).

EXAMPLE 12

To a solution of 1.20 g (3.59 mmol) of [1R-[1α(R*),3β,4α,7aα]]-[[octahydro-7a-methyl-1-(1-methyl-3-butynyl)-1H-inden-4-yl]oxy]-(1,1-dimethylethyl)dimethylsilane in 40 mL of dry tetrahydrofuran at −75° C. was added dropwise 3.70 mL (5.92 mmol) of 1.6M butyllithium in hexane. After stirring for 30 minutes at 75° C., hexafluoroacetone gas was bubbled into the reaction mixture for 10 minutes. The mixture was stirred at −75° C. for 25 minutes then quenched by addition of 1:1 mixture of 1M aqueous potassium tartrate and 2M aqueous KHCO$_3$ at 0° C. The mixture was stirred at 25° C. for 1 hour then extracted with methylene chloride. The organic phase was washed with the same salt mixture, dried (Na$_2$SO$_4$) and evaporated to dryness. The residue was chromatographed on silica gel (40–63μ) using 5% ethyl acetate/hexane as eluent to give 1.78 g (99%) of [1R-[1α(R*),3β,4α,7aα]]-1,1-bis(trifluoromethyl)-5-[[(4-1,1-dimethylethyl)-dimethylsilyl]-oxy]octahydro]-7a-methyl-1H-inden-1-yl]-2-pentyn-1-ol as an oil: $[\alpha]_D^{25} +34.4°$ (c 0.42, CHCl$_3$).

EXAMPLE 13

To a solution of 1.51 g (3.02 mmol) of [1R-[1α(R*),3β,4α,7aα]]-1,1-bis(trifluoromethyl)-5-[[(4-1,1-dimethylethyl)dimethylsilyl]oxy]octahydro]-7a-methyl-1-H-inden-1-yl]-2-pentyn-1-ol in 17 mL of acetonitrile and 15 mL of dry tetrahydrofuran was added 13.4 mL of 48% hydrofluoric acid. The mixture was stirred at 25° C. for 1.5 hours and diluted with water. The mixture was extracted with methylene chloride. The organic phase was washed with saturated aqueous NaHCO$_3$, dried (Na$_2$SO$_4$), and evaporated to dryness. The residue was chromatographed on silica gel (40–63μ) using 1:3 ethyl acetate-hexane as eluent to yield 1.16 g (99%) of [1R-[1α(R*),3β,4α,7aα]]-octahydro-1-[5-hydroxy-6-trifluoro-5-(trifluoromethyl)-1-methyl-3-hexynyl]-7a-methyl-1H-inden-4-ol as an oil: $[\alpha]_D^{25} +29.0°$ (c 0.57, CHCl$_3$).

EXAMPLE 14

To a solution of 0.200 g (0.518 mmol) of [1R-[1α(R*),3β,4α,7aα]]-octahydro-1-[5-hydroxy-6-trifluoro-5-(trifluoromethyl)-1-methyl-3-hexynyl]-7a-methyl-1H-inden-4-ol in 8 mL of dry methylene chloride was added 0.304 g (3.71 mmol) of anhydrous sodium acetate and 0.610 g (2.02 mmol) of 2',2'-bipyridinium chlorochromate (97%). The mixture was stirred at 25° C. for 2 hours. Then 0.305 g (1.01 mmol) of 2',2'-bipyridinium chlorochromate (97%) was supplemented and the mixture was stirred for another 1 hour and 50 minutes. After addition of 1.1 mL of 2-propanol, the mixture was diluted with water and extracted with 1:1 ethyl acetate-ether. The organic phase was washed with water, brine, dried (Na$_2$SO$_4$), and evaporated to dryness. The residue was chromatographed on silica gel (40–63μ) using 1:1 ethyl acetate-hexane to give [1R-[1α(R*),3aβ,7aα]]-octahydro-1-[5-hydroxy-6-trifluoro-5-(trifluoromethyl)-1-methyl-3-hexynyl]-7a-methyl-4H-inden-4-one as a glass: [α]$_D^{23}$ +2.3° (c 0.48, CHCl$_3$).

EXAMPLE 15

To a solution of 181 mg (0.289 mmol) of [3S-(1Z,3α,5β)]-[2-[3,5-bis[[(1,1-dimethylethyl)dimethylsilyl]oxy]-2-methylenecyclohexylidene]ethyl]diphenylphosphine oxide in 3.5 mL of dry tetrahydrofuran at −75° C. was added 0.164 mL (0.263 mmol) of 1.6M butyllithium in hexane. After stirring for 6 minutes, a solution of 40 mg (0.10 mmol) of [1R-[1α(R*),3aβ,7aα]]-octahydro-1-[5-hydroxy-6-trifluoro-5-(trifluoromethyl)-1-methyl-3-hexynyl]-7a-methyl-4H-inden-4-one in 2.5 mL of dry tetrahydrofuran was added dropwise. The mixture was stirred at −75° C. for 1 hour and 15 minutes and quenched by addition of 1:1 mixture of 1M aqueous potassium sodium tartrate and 2M aqueous KHCO$_3$. The mixture was extracted with ethyl acetate. The organic phase was washed with brine, dried (Na$_2$SO$_4$), and evaporated to dryness. The residue was chromatographed on silica gel (40–63μ) using 1:5 ethyl acetate-hexane as eluent to yield 65 mg (87%) of (1α,3β,5Z,7E)-1,3-bis[[(1,1-dimethylethyl)dimethylsilyl]oxy]-26,26,26,27,27,27-hexafluoro-9,10-secocholesta-5,7,10(19)-trien-23-yne-25-ol as a glass: [α]$_D^{23}$+38.8° (c 0.17, CHCl$_3$).

EXAMPLE 16

To a solution of 60 mg (0.080 mmol) of (1α,3β,5Z,7E)-1,3-bis[[(1,1-dimethylethyl)dimethylsilyl]oxy]-26,26,26,27,27,27-hexafluoro-9,10-secocholesta-5,7,10(19)-trien-23-yn-25-ol in 3 mL of tetrahydrofuran was added 0.58 mL (0.58 mmol) of 1M solution of 1M tetrabutylammonium fluoride in tetrahydrofuran. The mixture was stirred at 25° C. for 21 hours. After addition of 2 mL of half saturated aqueous NaHCO$_3$, the mixture was stirred at 25° C. for 15 minutes then extracted with ethyl acetate. The organic phase was washed with half saturated aqueous NaHCO$_3$, brine and dried (Na$_2$SO$_4$). The solution was evaporated to dryness and the residue was chromatographed on silica gel (40–63μ) to afford 41 mg (98%) of 1α,25-dihydroxy-26,26,26,27,27,27-hexafluoro-23-yne-cholecalciferol as a foamy glass: [α]$_D^{23}$+52.0° (c 0.15, MeOH).

EXAMPLE 17

To a solution of 0.292 g (0.645 mmol) of [S-(Z)]-[2-[5-[[(1,1-dimethylethyl)dimethylsilyl]oxy]-2-methylenecyclohexylidene]ethyl]diphenylphosphine oxide in 6.8 mL of dry tetrahydrofuran at −75° C. was added dropwise 0.366 mL (0.586 mmol) of 1.6M butyllithium in hexane. After stirring for 6 minutes, a solution of 89 mg (0.23 mmol) of [1R-[1α(R*),3aβ,7aα]]-octahydro-1-[5-hydroxy-6-trifluoro-5-(trifluoromethyl)-1-methyl-3-hexynyl]-7a-methyl-4H-inden-4-one in 6.6 mL of dry tetrahydrofuran was added dropwise. The mixture was stirred at −75° C. for 1 hour and 15 minutes and quenched by addiion of 1:1 mixture of 1M aqueous potassium sodium tartrate and 2M aqueous KHCO$_3$. The mixture was extracted with ethyl acetate. The organic phase was washed with brine, dried (Na$_2$SO$_4$), and evaporated to dryness. The residue was chromatographed on silica gel (40–63μ) using 1:5 ethyl acetate-hexane to give 118 mg (82%) of (3β,5Z,7E)-3-[[(1,1-dimethylethyl)dimethylsilyl]oxy]-26,26,26,27,27,27-hexafluoro-9,10-secocholesta-5,7,10(19)-trien-23-yne-25-ol as a glass: [α]$_D^{23}$+65.0° (c 0.18, CHCl$_3$).

EXAMPLE 18

To a solution of 0.113 g (0.183 mmol) of 3β,5Z,7E)-3-[[(1,1-dimethylethyl)dimethylsilyl]oxy]-26,26,26,27,27,27-hexafluoro-9,10-secocholesta-5,7,10(19)-triene-23-yne-25-ol in 5 mL of dry tetrahydrofuran was added 1.0 mL (1.0 mmol) of 1M tetrabutylammonium fluoride in tetrahydrofuran. The mixture was stirred at 25° C. for 16 hours. After addition of 3.5 mL of half saturated aqueous NaHCO$_3$, the mixture was stirred at 25° C. for 15 minutes then extracted with ethyl acetate. The organic phase was washed with half saturated aqueous NaHCO$_3$, brine and dried (Na$_2$SO$_4$). The solution was evaporated to dryness and the residue was chromatographed on silica gel (40–63μ) using 1:1 ethyl acetate-hexane to afford 79 mg (86%) of 25-hydroxy-26,26,26,27,27,27-hexafluoro-23-yne-cholecalciferol as a foamy glass: [α]$_D^{23}$+73.7° (c 0.19, MeOH).

EXAMPLE 19

To a solution of 0.243 g (0.537 mmol) of [S-(Z)]-[2-[5-[[(1,1-dimethyl)dimethylsilyl]oxy]-2-methylenecyclohexylidene]ethyl]diphenylphosphine oxide (Toh, H. T. and Okamura, W. H. *J. Org. Chem.* 1983, 48, 1416) in 5 mL of dry tetrahydrofuran was added dropwise 0.299 mL (0.478 mmol) of 1.6M butyllithium in hexane. After stirring for 6 minutes, a solution of 0.112 g (0.3321 mmol) of [1R-[1α,3aβ,7aα]octahydro-1]-1,5,5-trimethyl-5-[(trimethylsilyl)oxy]-3-pentynyl[-7a-methyl-4H-inden-4-one in 5.4 mL of dry tetrahydrofuran was added dropwise. The mixture was stirred at 75° C. for 1 hour and 5 minutes and quenched by addition of 1:1 mixture of 1M aqueous potassium sodium tartrate and 2M aqueous KHCO$_3$. The mixture was extracted with ethyl acetate. The organic phase was washed with saturated brine, dried (Na$_2$SO$_4$), and evaporated to dryness. The residue was chromatographed on silica gel using 1:15 ethyl acetate-hexane to give 0.174 g (93%) of (3β,5Z,7E)-3-[[(1,1-dimethylethyl)dimethylsilyl]oxy]-9,10-secocholesta-5,7,10(19)-trien-23-yne-25-yl]oxy]-trimethylsilane as a glass: [α]$_D^{23}$+79.2° (c, 0.24, CHCl$_3$).

EXAMPLE 20

To a solution of 0.167 g (0.286 mmol) of (3β,5Z,7E)-3-[[( 1,1-dimethyl)dimethylsilyl]oxy]-9,10-secocholesta-5,7,10(19-trien-23-yne-25-yl]oxy]trimethylsilane in 10 mL of dry tetrahydrofuran was added 2.6 mL (2.6 mmol) of 1M tetra-n-butylammonium fluoride in tetrahydrofuran. The mixture was stirred at 23° C. for 5 hours. After addition of 3.3 mL of half saturated aqueous NaHCO$_3$, the mixture was stirred at 23° C. for 15 minutes. The mixture was diluted with water and extracted with ethyl acetate. The organic phase was washed with water, brine and dried (Na$_2$SO$_4$). The solution was evaporated to dryness and the residue was chromatographed on silica gel using 1:1 ethyl acetate-hexane to afford 0.104 g (94%) of (3β,5Z,7E)-9,10-secocholesta-5,7,10(19)-triene-23-yne-3,25-diol as a foamy glass: [α]$_D^{23}$+98.8° (c 0.16, MeOH).

EXAMPLE 21

| CAPSULE FORMULATION | | |
|---|---|---|
| | mg/cap | |
| 1α,25-dihydroxy-23-yne-24,24,26,26,26,27,27,27-hexafluorocholecalciferol | 0.000250 | 0.002 |
| Fractionated Coconut Oil | 199.995 | 199.990 |
| Butylated Hydroxy Anisol | 0.01 | 0.01 |
| Ascorbyl Palmitate | 1.0 | 1.0 |

1. Dissolve the drug in Fractionated Coconut Oil.
2. Add Butylated Hydroxy Anisol and Ascorbyl Palmitate to the solution in Step 1 and dissolve.
3. Fill in Soft Gelatin Capsules.

EXAMPLE 22

| CAPSULE FORMULATION | | |
|---|---|---|
| | mg/cap | |
| 1α,25-dihydroxy-23-yne-26,26,26,27,27,27-hexafluorocholecalciferol | 0.00025 | 0.002 |
| Fractionated Coconut Oil | 199.995 | 199.990 |
| Butylated Hydroxy Anisol | 0.01 | 0.01 |
| Ascorbyl Palmitate | 1.0 | 1.0 |

1. Dissolve the drug in Fractionated Coconut Oil.
2. Add Butylated Hydroxy Anisol and Ascorbyl Palmitate to the solution in Step 1 and dissolve.
3. Fill in Soft Gelatin Capsules.

We claim:

1. A compound of the formula

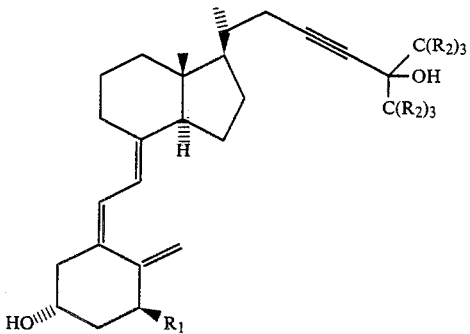

wherein $R_1$ is hydrogen or hydroxy and $R_2$ is hydrogen or fluorine.

2. A compound in accordance with claim 1, wherein $R_2$ is fluorine.

3. The compound in accordance with claim 2, 1α,25-dihydroxy-23-yne-26,26,26,27,27,27-hexafluorocholecalciferol.

4. The compound in accordance with claim 2, 25-hydroxy-23-yne-26,26,26,27,27,27-hexafluorocholecalciferol.

5. A compound in accordance with claim 1, wherein $R_2$ is hydrogen.

6. The compound in accordance with claim 5, 1α,25-dihydroxy-23-yne-cholecalciferol.

7. The compound in accordance with claim 5, 25-hydroxy-23-yne-cholecalciferol.

8. A composition comprising a pharmaceutically effective amount of a compound of the formula

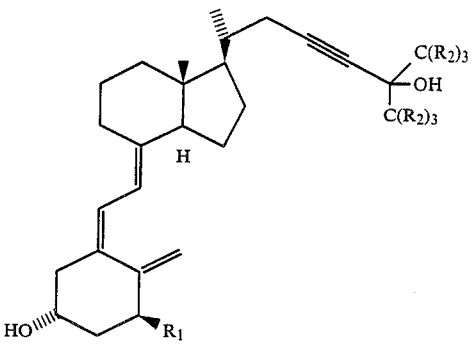

wherein $R_1$ is hydrogen or hydroxy and $R_2$ is hydrogen or fluorine, and a pharmaceutically acceptable carrier material.

9. A composition in accordance with claim 8 wherein $R_2$ is fluorine.

10. A composition in accordance with claim 9, wherein the compound of formula I is 1α,25-dihydroxy-23-yne-26,26,26,27,27,27-hexafluorocholecalciferol.

11. A method for treating disease states characterized by metabolic calcium deficiencies which comprises administering an effective amount of a compound of the formula

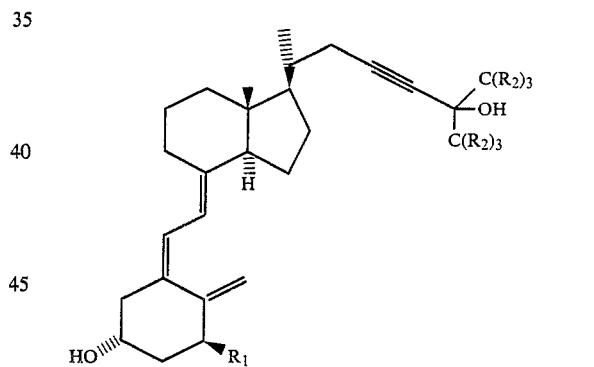

wherein $R_1$ is hydrogen or hydroxy and $R_2$ is hydrogen or fluorine.

12. A method in accordance with claim 11, wherein the disease state characterized by metabolic calcium deficiency is osteoporosis.

13. A method in accordance with claim 12, wherein $R_2$ is fluorine.

14. A method in accordance with claim 13, wherein the compound of formula I is 1α,25-dihydroxy-23-yne-26,26,26,27,27,27-hexafluorocholecalciferol.

15. A method in accordance with claim 11, wherein the compound of formula I is administered in a dosage of from about 0.1 μg to about 2 μg.

* * * * *